(12) United States Patent
Zasloff et al.

(10) Patent No.: US 9,504,700 B2
(45) Date of Patent: Nov. 29, 2016

(54) METHODS AND COMPOSITIONS FOR STIMULATION AND ENHANCEMENT OF REGENERATION OF TISSUES

(71) Applicant: MOUNT DESERT ISLAND BIOLOGICAL LABORATORY, Salisbury Cove, ME (US)

(72) Inventors: Michael Alan Zasloff, Merion, PA (US); Viravuth Pho Yin, Trenton, ME (US); Kevin B. Strange, Lamoine, ME (US)

(73) Assignee: Mount Desert Island Biological Laboratory, Salisbury Cove, ME (US)

( * ) Notice: Subject to any disclaimer, the term of this patent is extended or adjusted under 35 U.S.C. 154(b) by 0 days.

(21) Appl. No.: 14/137,259

(22) Filed: Dec. 20, 2013

(65) Prior Publication Data

US 2014/0179658 A1   Jun. 26, 2014

Related U.S. Application Data

(60) Provisional application No. 61/740,291, filed on Dec. 20, 2012.

(51) Int. Cl.
*A61K 31/56* (2006.01)
*A61K 31/575* (2006.01)
*A61K 45/06* (2006.01)

(52) U.S. Cl.
CPC ............. *A61K 31/575* (2013.01); *A61K 45/06* (2013.01)

(58) Field of Classification Search
CPC . A61K 31/575; A61K 2300/00; A61K 45/06
See application file for complete search history.

(56) References Cited

U.S. PATENT DOCUMENTS

| 5,847,172 | A | * | 12/1998 | Zasloff ................... A61K 31/56 552/521 |
| 6,143,738 | A | | 11/2000 | Zasloff |
| 2008/0058300 | A1 | * | 3/2008 | McLane et al. ............... 514/182 |
| 2009/0105204 | A1 | | 4/2009 | Zasloff et al. |
| 2011/0123624 | A1 | | 5/2011 | Zasloff |

FOREIGN PATENT DOCUMENTS

| WO | WO 98/27106 | 6/1998 |
| WO | WO 2004/018706 A2 | 3/2004 |
| WO | WO 2008/110941 A2 | 9/2008 |
| WO | WO 2009/091609 | 7/2009 |

OTHER PUBLICATIONS

WebMD http://www.webmd.com/heart-disease/guide/heart-disease-heart-attacks?print=true, access on Apr. 2, 2015.*
Cingolani, MD, et al., Sodium-Hydrogen Exchanger . . . Hypertrophy; 2007 American Heart Association, Inc. 12 pages.*
Dallenbach, et al., Hepatellular Na+/H+ Exchange . . . Rat Live, 1994.*
Fliegel, et al. The Na+/H+ Exchanger: A Target for Cardiac Therapeutic Intervention; 2005 Bentham Publishers Ltd., pp. 1-13.*
Malo, et al. Physiological role and regulations of the Na+/H+ exchanger Can. J. Physicol Pharmacol. 84; pp. 1081-1095 (2006).*
Notification of Transmittal of the International Search Report and the Written Opinion of the International Searching Authority, or the Declaration, for International Appl. No. PCT/US13/77118, dated Apr. 15, 2014.
S. Akhter, et al., Squalamine, a novel cationic specifically . . . NHE3,1999; 1999 the American Physiological Society, pp. C136-C144.
L. Ceremuzynski, el al,, Low-Dose Glucose-Insulin-Potassium . . . Trial; Cardiovascular Drugs and Therapy 1999:13, pp. 191-200.
H.E. Cingolani, MD, et al., Sodium-Hydrogen Exchanger . . . Hypertrophy; 2007 American Heart Association, Inc. 12 pages.
A. Dallenbach, et al., Hepatellular $Na^+/H^+$ Exchange . . . Rat Liver Regeneration; 1994 American Association for the Study of Liver Diseases, pp. 1290-1301.
S.E. Inzucchi, MD, et al., Insulin-Sensitizing Antihyperglycemic . . . Infarction; Diabetes Care, vol. 28, No. 7, Jul. 2005, pp. 1680-1689.
M. Karmazyn, et al. The $Na^+/H^+$ Exchanger: A Target for Cardiac Therapeutic Intervention; 2005 Bentham Publishers Ltd., pp. 1-13.
M. E. Malo, et al. Physiological role and regulations of the $Na^+/H^+$ exchanger Can. J. Physicol Pharmacol. 84; pp. 1081-1095 (2006).
National Heart, Lung, and Blood Institute, How to prevent and Control Coronary Heart Disease Risk Factors, NHLBI, NIH; Oct. 23, 2015, three pages.
UK Prospective Diabetes Study (UKPDS) Group, Intensive blood-glucose control with sulphonylureas or . . . diabetes; The Lancet—vol. 352, Sep. 12, 1998, 17 pages.
Zhaohong Qin, et al. Functional properties of Claramine: A Novel PTP1B . . . compound; 2015 Elsevier—Biochemical and Biophysical Research Communications, 7 pgs.
Stephan J. Reshkin, et al., $Na^+/H^+$ exchanger-dependent intracellular alkalinization . . . phenotypes; The FASEB Journal, vol. 14,Nov. 2000, pp. 2185-2197.
Lin Xue, et al., Trefoil Factor 2 Requires Na/H Exchanger 2 . . . Repair; Journal of Biological Chemistry, Nov. 4, 2011, 11 pgs.
Akinori Yanaka, et al., EGF promotes gastric mucosal . . . Cells; AJP Gastrointest Liver Physiol, vol. 282, May 2002, pp. 866-8761.
Supplementary European Search Report for International Appl. No. EP 13 86 3996 dated May 12, 2016.

* cited by examiner

*Primary Examiner* — Jean Cornet
(74) *Attorney, Agent, or Firm* — Preti Flaherty Beliveau & Pachios LLP

(57) ABSTRACT

Methods and pharmaceutical compositions are provided for enhancing or stimulating regeneration of a tissue in a subject. In one aspect, the invention provides a method including administering to a subject in need thereof a therapeutically effective amount of an aminosterol or a pharmaceutically acceptable salt thereof to stimulate or enhance regeneration of a tissue. In another aspect, the invention provides a method including administering to a subject a therapeutically effective amount of an aminosterol or a pharmaceutically acceptable salt thereof to stimulate or enhance regeneration of a tissue to treat or prevent a disease, disorder, trauma, or condition resulting from an injury of the tissue. In an additional aspect, the invention provides a pharmaceutical composition comprising a therapeutically effective amount of an aminosterol to stimulate or enhance regeneration of a tissue.

9 Claims, 8 Drawing Sheets

METHODS AND COMPOSITIONS FOR STIMULATION AND ENHANCEMENT OF REGENERATION OF TISSUES

STATEMENT REGARDING FEDERALLY SPONSORED RESEARCH OR DEVELOPMENT

N/A

BACKGROUND OF THE INVENTION

Tissue regeneration in humans is extremely limited and constitutes a major challenge to the repair of damaged limb function. Injured tissues are able to heal by regeneration, by repair, or by a combination of these processes. Regeneration results in the re-establishment of the original tissue structure and function. Bodily structures comprised of composite tissues, such as a limb or digit, or an appendage, are made of numerous cell types arranged in an organized and iterative structure that is preserved from individual to individual. When composite tissues or bodily structures comprised of composite tissues are injured, regeneration requires the coordinated growth, and interactions of numerous cell types within the composite tissues to regenerate a bodily structure that effectively is indistinguishable from the original. Tissue regeneration is a rapidly developing field of biomedical research that aims at regenerating damaged tissues. But in mammals and other higher organisms, there is a failure of regeneration of composite or complex tissues. Therefore, there is a need for methods and compositions to regenerate damaged or injured tissue and limbs after injury.

SUMMARY OF THE INVENTION

Methods and compositions are provided for enhancing or stimulating regeneration of tissues, including as non-limiting examples, limbs or organs in a subject. As a result of such enhancement or stimulation, certain medical benefits are achieved including the treatment of tissue injured by disease, disorders, trauma or other conditions where regeneration of the injured tissues, such as those involving the liver, skin, soft tissues and muscle, heart, nervous system, intestines, hematopoietic and vascular system, would be beneficial. The objective of the invention is to enhance the rate and healing capacity of injured tissues. In certain aspects, the method of the invention includes identifying a subject having a tissue injury including, for non-limiting examples, a limb or organ injury, and administering a therapeutically effective amount of an aminosterol such as, for example, a MSI-1436 or a pharmaceutically acceptable salt thereof that enhances or stimulates tissue regeneration in the subject.

It has been discovered that administering to a subject a therapeutically effective amount of an aminosterol such as, for example, MSI-1436 or pharmaceutically acceptable salt thereof, enhances or stimulates regeneration of an injured issue to treat or prevent a disease, disorder, trauma or other condition. Subjects preferably can include mammals, and more preferably can include humans. Targeted issue can be selected from liver tissue, skin soft tissues, skeletal muscle, cardiac muscle, vascular tree, central and peripheral nervous system, gastrointestinal tract, exocrine and endocrine pancreas, skeletal system, and hematopoietic tissues. The invention shows that therapeutically effective amounts of MSI-1436 preferably including from about 0.1 to about 20-mg/kg-body weight (equivalent to about 0.07 mg/kg to about 2.67 mg/kg body weight in a human) promotes the regeneration of injured tissue including, for a non-limiting example, limbs or organs.

In one aspect, the invention provides a method including the step of administering to a subject in need thereof a therapeutically effective amount of an aminosterol or a pharmaceutically acceptable salt thereof to stimulate or enhance regeneration of a tissue. In one embodiment, the invention provides prior to the administering step, identifying a subject having an injury of the tissue. In another embodiment, the invention provides a method wherein the tissue is selected from the group consisting of a liver tissue, a skin soft tissue, a skeletal muscle tissue, a cardiac muscle tissue, a vascular tree tissue, a central nervous system tissue, a peripheral nervous system tissue, a gastrointestinal tract tissue, an exocrine pancreas tissue, an endocrine pancreas tissue, a skeletal system tissue, and an hematopoietic tissue. In yet other embodiments, the invention provides a method, wherein the aminosterol is MSI-1436 or wherein the aminosterol is an isomer of MSI-1436.

In another embodiment, the invention provides a method wherein the aminosterol includes a sterol nucleus and a polyamine, attached at any position on the sterol, such that the aminosterol exhibits a net charge of at least +1, the charge being contributed by the polyamine. In yet another embodiment, the invention provides a method wherein the aminosterol is modified to include at least one of the following: a substitution of the sulfate, wherein the substitution is selected from the group consisting of a sulfonate, a phosphate, a carboxylate, and an anionic moiety, and wherein the substitution is chosen to circumvent metabolic removal of the sulfate moiety and oxidation of the cholesterol side chain; a replacement of a hydroxyl group by a non-metabolizable polar substituent to prevent its metabolic oxidation or conjugation; and a substitution of at least one ring hydrogen atom to prevent oxidative or reductive metabolism of the steroid ring system. In a further embodiment, the invention provides a method wherein the non-metabolizable polar substituent is a fluorine atom. In yet a further embodiment, the invention provides a method wherein the aminosterol is a derivative of MSI-1436 modified through medical chemistry to improve at least one of bio-distribution, ease of administration, metabolic stability, and a combination of at least two thereof.

In addition, the invention provides a method wherein the therapeutically effective amount of MSI-1436 is from about 0.07 mg/kg to about 2.67 mg/kg body weight in a human. In another embodiment, the invention provides a method wherein the therapeutically effective amount of MSI-1436 is administered in combination with at least one additional active agent to achieve an additive or synergistic effect. In yet another embodiment, the invention provides a method wherein the active agent is administered concomitantly, as an admixture, separately and simultaneously, separately and concurrently, or separately and sequentially. In a further embodiment, the invention provides a method wherein a therapeutically effective amount of aminosterol is administered in the form of a liquid, a capsule, a tablet, intravenously, intraperitoneally, inhaled, or topically. In yet a further embodiment, the invention provides a method wherein the subject is a mammal. In another embodiment, the invention provides a method wherein the subject is a human.

In another aspect, the invention provides a method including administering to a subject a therapeutically effective amount of an aminosterol or a pharmaceutically acceptable salt thereof to stimulate or enhance regeneration of a tissue to treat or prevent a disorder, disease, or condition resulting from an injury of the tissue. In one embodiment, the method includes prior to the administering step, identifying the subject having the disorder, disease, trauma or condition resulting from an injury of the tissue. In another embodiment, the invention provides a method wherein the tissue is selected from the group consisting of: a liver tissue, a skin soft tissue, a skeletal muscle tissue, a cardiac muscle tissue, a vascular tree tissue, a central nervous system tissue, a peripheral nervous system tissue, a gastrointestinal tract tissue, a exocrine pancreatic tissue, an endocrine pancreatic tissue, a skeletal system tissue, and a hematopoietic tissue. In yet another embodiment, the invention provides a method wherein the aminosterol is MSI-1436. In a further embodiment, the invention provides a method wherein the aminosterol is an isomer of MSI-1436. In an additional embodiment, the invention provides a method wherein the aminosterol comprises a sterol nucleus and a polyamine, attached at any position on the sterol, such that the aminosterol exhibits a net charge of at least +1, the charge being contributed by the polyamine. In yet a further embodiment, the invention provides a method wherein the aminosterol is modified to include at least one of the following: a substitution of the sulfate, wherein the substitution is selected from the group consisting of a sulfonate, a phosphate, a carboxylate, and an anionic moiety, and wherein the substitution is chosen to circumvent metabolic removal of the sulfate moiety and oxidation of the cholesterol side chain; a replacement of a hydroxyl group by a non-metabolizable polar substituent to prevent its metabolic oxidation or conjugation; and a substitution of at least one ring hydrogen atom to prevent oxidative or reductive metabolism of the steroid ring system. In another embodiment, the invention provides a method wherein the non-metabolizable polar substituent is a fluorine atom.

In an additional embodiment, the invention provides a method wherein the aminosterol is a derivative of MSI-1436 modified through medical chemistry to improve at least one of bio-distribution, ease of administration, metabolic stability, and a combination of at least two thereof. In another embodiment, the invention provides a method wherein the therapeutically effective amount of MSI-1436 is from about 0.07 mg/kg to about 2.67 mg/kg body weight in a human. In yet another embodiment, the invention provides a method wherein a therapeutically effective amount of MSI-1436 is administered in combination with at least one additional active agent to achieve an additive or synergistic effect. In a further embodiment, the invention provides a method wherein the active agent is administered concomitantly, as an admixture, separately and simultaneously, separately and concurrently, or separately and sequentially. In yet a further embodiment, the invention provides a method wherein the therapeutically effective amount of aminosterol is administered in the form of a liquid, capsule, tablet, intravenously, intraperitoneally, inhaled, or topically. In yet a further embodiment, the invention provides a method wherein the subject is a mammal. In an additional embodiment, the invention provides a method wherein the subject is a human.

In another aspect, the invention provides a pharmaceutical composition including a therapeutically effective amount of an aminosterol to stimulate or enhance regeneration of a tissue. In one embodiment, the invention provides the aminosterol in a range from about 0.07 mg/kg to about 2.67 mg/kg body weight in a human. In an embodiment, the invention provides a kit including the pharmaceutical composition. In another embodiment, the invention provides a composition wherein the aminosterol is MSI-1436. In yet another embodiment, the invention provides a composition wherein the aminosterol is an isomer of MSI-1436. In a further embodiment, the invention provides a composition wherein the aminosterol comprises a sterol nucleus and a polyamine, attached at any position on the sterol, such that the aminosterol exhibits a net charge of at least +1, the charge being contributed by the polyamine. In yet a further embodiment, the invention provides a composition wherein the aminosterol is modified to include at least one of the following: a substitution of the sulfate, wherein the substitution is selected from the group consisting of a sulfonate, a phosphate, a carboxylate, and an anionic moiety, and wherein the substitution is chosen to circumvent metabolic removal of the sulfate moiety and oxidation of the cholesterol side chain; a replacement of a hydroxyl group by a non-metabolizable polar substituent to prevent its metabolic oxidation or conjugation; and a substitution of at least one ring hydrogen atom to prevent oxidative or reductive metabolism of the steroid ring system. In an additional embodiment, the invention provides a composition wherein the non-metabolizable polar substituent is a fluorine atom.

In another embodiment, the invention provides a composition wherein the aminosterol is a derivative of MSI-1436 modified through medical chemistry to improve at least one of bio-distribution, ease of administration, metabolic stability, and a combination of at least two thereof. In yet another embodiment, the invention provides a composition wherein the composition includes at least one additional active agent to achieve an additive or synergistic effect.

These and other features, aspects, and advantages of the present invention will become better understood with regard to the following description and appended claims.

BRIEF DESCRIPTION OF THE DRAWINGS

These and other advantageous aspects of the invention will be evident from the following detailed description, which should be considered in conjunction with the attached drawings, wherein.

DETAILED DESCRIPTION

Figure 1:
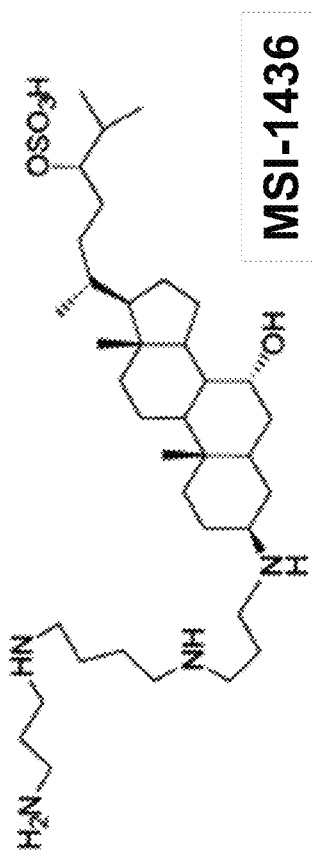
FIG. 1 illustrates the molecular structure of aminosterol MSI-1436.

The present invention is directed to methods of enhancing or stimulating regeneration of tissues in a subject. Such tissues can include, as non-limiting examples, limbs or organs. The invention is unanticipated and based on the discovery of a previously unknown property of the aminosterol MSI-1436. The utility afforded by this invention includes all applications in which stimulation or enhancement of regeneration of a tissue including, for a non-limiting example, composite or complex tissues, would have benefit. These applications include, for non-limiting examples, conditions such soft tissue injury involving skin, dermis, or muscle; hepatic regrowth, following partial hepatectomy or in the setting of cirrhosis; cardiac muscle, in the setting of ischemic injury; the nervous system, following traumatic injury; the regrowth of amputated limbs; the possible regeneration of islet cells in diabetes mellitus; the recovery of intestinal epithelium in the setting of inflammatory bowel disease.

1. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The terms "animal," "patient," or "subject" as used herein, mean any animal (e.g., mammals, including, but not limited to humans, primates, dogs, cattle, cows, horses, kangaroos, pigs, sheep, goats, cats, rabbits, rodents), transgenic non-human animals, fish, amphibians, not limited to frogs, and salamanders, reptiles, other vertebrates and invertebrates and the like, which are to be the recipient of a particular treatment. Typically, the terms "animal" "subject" and "patient" are used interchangeably herein in reference to a human subject. The preferred animal, patient, or subject is a mammal and more preferably a human.

As used herein, the terms "administer", "administering", and "administered" refer to providing the drug to the subject being tested or treated. In certain embodiments, the aminosterol e.g., MSI-1436 is administered in the form of a liquid, capsule, tablet, intraperitoneally, subcutaneously, intravenously, inhaled, that is intranasally, or topically, but can include microinjection, and/or direct application to the injured tissue including, for non-limiting examples, an injured limb or organ.

The terms, "enhance", "enhancing", and "enhanced" as used herein refer to activities whose effects are greater than that which is observed in a control or an untreated group or subject. Enhanced activity may be measured in vivo or in cell culture studies.

The terms "growth", "grow", "grown", or "growing" as used herein, mean the growth of tissue, including but not limited to one or more tissues, limbs or organs, following an injury of the tissue resulting from a diseases, disorder, trauma or other condition and includes but is not limited to regeneration as described herein below.

The terms "injury of a tissue" and "tissue injury" as used herein, mean damage of a tissue that disrupts its physical structure resulting in the impairment of its function.

The terms "injury of a limb" and "limb injury" as used herein, mean damage of a limb such as, for non-limiting examples, a finger, arm or foot, that involves a trauma to any or all of the tissues included in the limb.

The terms "injury of an organ" and "organ injury" as used herein, mean damage of an organ that involves a trauma to any or all of the tissues includes in the organ.

The term, "kit" as used herein, means any manufacture (e.g., a package or container) including at least one reagent, e.g., an aminosterol such as MSI-1436. In certain embodiments, the manufacture may be promoted, distributed, or sold as a unit for performing the methods of the invention.

The terms, "regenerate," "regenerating," or "regeneration" as used herein mean the restoration of a tissue, including but not limited to one or more tissues, limbs or organs, to its original state following an injury of the tissue resulting from a disease, disorder, trauma or other condition.

As used herein, the terms "stimulate", "stimulating", "stimulated" refer to an activities whose effects are greater than that which is observed in a control or an untreated group. Stimulatory effects may be measured in vivo or in cell culture studies.

As used herein, the terms "therapeutic activity" or "activity" may refer to an activity whose effect is consistent with a desirable therapeutic outcome in humans, or to desired effects in non-human mammals or in other species or organisms.

The term "therapeutically effective amount" as used herein means an amount that achieves the intended therapeutic effect of enhancing or stimulating regeneration of a tissue, including but not limited to one or more tissues, limbs or organs, in a subject. The full therapeutic effect does not necessarily occur by administration of one dose and may occur only after administration of a series of doses. Thus, a therapeutically effective amount may be administered in one or more administrations per day for successive days.

The terms "treat" "treating", "treated" or "treatment" in a subject having an injury to a tissue resulting from a disease, disorder, trauma or other condition as used herein, mean taking steps to obtain beneficial or desired results, including clinical results. For purposes of this invention, beneficial or desired clinical results include, but are not limited to stimulating or enhancing regeneration of a tissue, including but not limited to one or more tissues, limbs or organs, in a subject.

The term "tissue" and "tissues" as used herein, refer to single, composite and/or complex tissues which can form, for non-limiting examples, a limb or an organ.

2. Overview

It has been discovered that an aminosterol such as MSI-1436, is a new therapy for tissue regeneration. The molecular structure of MSI-1436 is illustrated in FIG. 1. Specifically, MSI-1436 stimulates faster regeneration of missing limb and cardiac tissues by amplifying growth factor pathways important for tissue regeneration. Importantly, MSI-1436 treatment rescues genetically mediated defects in cardiomyocyte proliferation to normal levels. Certain embodiments are directed to identifying subjects having tissue injury and administering to the subject a therapeutically effective amount of an aminosterol such as MSI-1436 that enhances or stimulates tissue regeneration. In other embodiments, the invention is directed to pharmaceutical formulations comprising MSI-1436.

Vertebrate regeneration is robustly observed in a limited number of species, including fish, amphibian, and reptiles (K D Poss, Keating, & Nechiporuk, 2003; Sánchez Alvarado & Tsonis, 2006). In mammals, regenerative activity is observed in early fetal development, but becomes highly restricted to specific organs in post-natal life (Kenneth D Poss, 2010).

In particular the human liver is known to functionally regenerate after partial hepatectomy (Taub, 2004). The epithelial lining of the small and large bowel can be reconstituted after a severe inflammatory insult (Simons & Clevers, 2011); restoration of the blood forming tissues in the bone marrow occurs following ablative therapies. Other tissues in the post-natal human exhibit much less regenerative potential. Indeed, extensive soft tissue injury to a limb is repaired through a wound healing process that lays down scar tissue, rather than one that restores the prior tissue architecture. In no case is it possible regenerate an appendage in a post-natal human.

3. Background

MSI-1436 is a molecule similar in structure to squalamine but differing in the nature of the polyamine, that being a spermine in MSI-1436, and a spermidine in squalamine.

to involve inhibition of a lymphocyte-specific NHE by 1436, resulting in suppression of cytokine responsiveness, and subsequent depression of the capacity of the lymphocyte to support HIV replication (U.S. Pat. No. 5,763,430). Aminosterol MSI-1436, however, has an additional pharmacological property, not shared with squalamine, namely potent appetite suppression and promotion of dose-dependent weigh loss (U.S. Pat. No. 6,143,738; M Zasloff et al., 2001; Ahima et al., 2002). In addition, MSI-1436 corrected the diabetic phenotype in mice with leptin receptor lesions and leptin deficiency (Takahashi, Qi, Patel, & Ahima, 2004). Many of the metabolic effects of appear to a consequence of its activity on specific centers in the central nervous system (Bence et al., 2006).

The utility of MSI-1436 as an anti-infective has been demonstrated in vitro against bacteria and fungi (Rao et al., 2000) Like squalamine, MSI-1436 is a cationic amphipathic substance exhibiting an affinity for membranes composed of anionic phospholipids (Selinsky et al., 1998; Selinsky, Smith, Frangiosi, Vonbaur, & Pedersen, 2000). Like other such agents, including magainin and cationic antimicrobial peptides, MSI-1436 is believed to exert antimicrobial action by interacting electrostatically with the membranes of target microorganisms, which generally display anionic phospholipids on the membrane surface exposed to the environment, subsequently disturbing their functional integrity, and causing death of the targeted microbe (Michael Zasloff, 2002; Salmi et al., 2008; Sills et al., 1998).

The utility of MSI-1436 in vivo has been demonstrated in models of obesity (Lantz et al., 2010), diabetes (Takahashi et al., 2004), and hepatic steatosis (Lantz et al., 2010). No report of its capacity to stimulate regeneration has been previously described or demonstrated.

It has been reported that squalamine exerts its effects on human cells and tissues at the cellular level by displacing

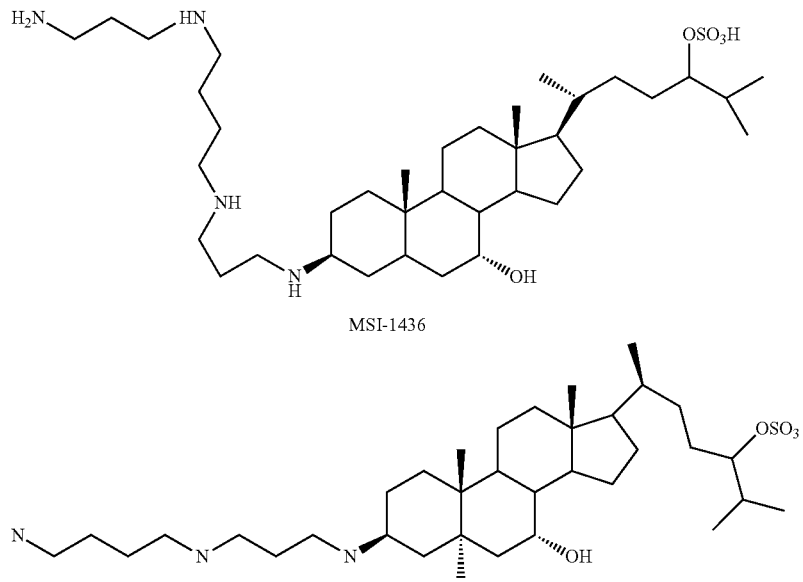

MSI-1436

Squalamine

Aminosterol MSI-1436 is an aminosterol isolated from the dogfish shark, which is structurally related to squalamine (U.S. Pat. No. 5,840,936; Rao et al., 2000). Aminosterol MSI-1436 exhibits antiviral activity against HIV in tissue culture (U.S. Pat. No. 5,763,430) via a mechanism proposed proteins bound electrostatically to negatively charged membranes, causing pleiotropic changes in the functional state of the cell (Alexander et al., 2011; Yeung et al., 2008; Sumioka, Yan, & Tomita, 2010; Michael Zasloff et al., 2011). It is believed that the fundamental mechanism of action of MSI-1436 also involves electrostatic interactions with negatively charged intracellular membranes, but the precise phospholipids targeted and the specific membranes onto which MSI-1436 localizes differ from squalamine.

At the cellular level MSI-1436 has been shown to inhibit a broadly acting tyrosine phosphatase PTP1B (Lantz et al., 2010). Specifically, MSI-1436 was shown to inhibit the activity of PTP1B in an in vitro enzyme assay (Lantz et al., 2010). In addition, the addition of MSI-1436 to hepatoma cells was shown to increase the level of phosphorylation of the insulin receptor, and known target of PTP1B (Lantz et al., 2010). Administration of MSI-1436 to a mouse, resulted in an increase in the recovery of phosphorylated insulin receptor from the hypothalamus, associated with the administration of insulin (Lantz et al., 2010). Furthermore the levels of phosphorylated STAT3, a downstream component of the insulin receptor circuit, were increased after both insulin administrations, compared to the extent observed following administration of insulin alone (Lantz et al., 2010).

It has been reported that squalamine exerts its effects at the cellular level by displacing proteins bound electrostatically to negatively charged membranes, causing pleiotropic changes in the functional state of the cell (Alexander et al., 2011; Sumioka et al., 2010; Yeung et al., 2008; Michael Zasloff et al., 2011). With respect to the disclosed invention, and without being bound by theory, it is believed that aminosterols, such as Aminosterol MSI-1436, enter certain tissues (via specific transporters) and influence intracellular signaling by the electrostatic mechanism proposed.

MSI-1436 is known to inhibit PTP1B, a phosphatase that normally "turns off" the insulin receptor after it has been occupied by insulin, and thereby "quiets" the insulin response. PTP1B is known to act on other tyrosine kinase receptors in addition to the insulin receptor. The known targets of PTP1B include, in addition to the insulin receptor, the insulin related growth factor receptor (IGFR), the epidermal growth factor receptor (EGFR), the fibroblast growth factor receptor (FGFR), colony stimulating growth factor receptor (CSFR), hepatocyte stimulating factor receptor (HSFR), and platelet derived growth factor receptor (PDGFR).

PTP1B is known to be localized within the cellular endoplasmic reticulum (Frangioni, Beahm, Shifrin, Jost, & Neel, 1992). It is believed to access the receptor target by a mechanism that involves the "kissing" of the cytoplasmic face of the plasma membrane, in which the phosphorylated site is localized, by a "ruffle" of the endoplasmic reticulum containing PTP1B (Frangioni et al., 1992). Thus, the physical contact of PTP1B, present on the endoplasmic reticulum, with the phosphorylated receptor present on the cytoplasmic face of the plasma membrane, is required for de-phosphorylation to occur.

Taken together, these properties of PTP1B suggest that MSI-1436 likely displaces PTP1B from the endoplasmic reticulum. We presume that MSI-1436 binds to the endoplasmic reticulum, neutralizes the electrostatic interactions that are involved in the attachment of PTP1B, leading to its release, and its ultimate "inactivation". In this scenario, inactivation is a direct consequence of its displacement from an intracellular site in which it normally operates, as opposed to a direct effect on the enzyme itself.

Vertebrate regeneration is robustly observed in a limited number of species, including fish, amphibian, and reptiles (K D Poss, Keating, & Nechiporuk, 2003; Sanchez Alvarado & Tsonis, 2006). In mammals, regenerative activity is observed in early fetal development, but becomes highly restricted to specific organs in post-natal life (Kenneth D Poss, 2010).

In particular the human liver is known to functionally regenerate after partial hepatectomy (Taub, 2004). The epithelial lining of the small and large bowel can be reconstituted after a severe inflammatory insult (Simons & Clevers, 2011); restoration of the blood forming tissues in the bone marrow occurs following ablative therapies. Other tissues in the post-natal human exhibit much less regenerative potential. Indeed, extensive soft tissue injury to a limb is repaired through a wound healing process that lays down scar tissue, rather than one that restores the prior tissue architecture. There are currently no known cases that we can identify which show regeneration of an appendage in a post-natal human.

The zebrafish is known to have the capacity to robustly regenerate various tissues and organs and has become a well characterized model for the systematic study of the regenerative process in vertebrates (K D Poss et al., 2003; Kenneth D Poss, 2010). In particular, regeneration of the heart and liver has been extensively explored in this animal (Curado & Stainier, 2010; Kenneth D Poss, Wilson, & Keating, 2002). Regrowth of the amputated tail fin has been used a model for the study of the regrowth of a vertebrate appendage. Recent reports have highlighted the roles of several well studied growth factor pathways in the regenerative processes of the zebrafish, including those of Wnts, insulin related growth factor, retinoic acid, TGFβ and fibroblast related growth factor (Chablais & Jazwinska, 2010; Jazwinska, Badakov, & Keating, 2007; Yin et al., 2008; Blum & Begemann, 2012; Lee, Grill, Sanchez, Murphy-Ryan, & Poss, 2005; Stoick-Cooper et al., 2007).

Although the precise mechanism by which MSI-1436 exerts its unprecedented and unanticipated effects on tissue including as non-limiting examples limb or organ regeneration in the vertebrate are not as understood, without being bound by theory, it is speculated that (1) since the regenerative process involves the action of numerous growth factors that utilize receptors that are phosphorylated by tyrosine receptor kinases, and (2) that PTP1B normally turns off these receptors after activation, and (3) that MSI-1436 inhibits PTP1B, MSI-1436 potentiates the activity of the growth factors that are engaged in the regenerative process. By permitting the activated receptor to remain active for a longer period of time than normal, the magnitude of the biological response to the cognate growth factor would be enhanced. In a sense the "gain" on the system would be increased. Since the "master" regulators of the repair process are these growth factors, and since the spatiotemporal unfolding must require precise elaboration of these growth factors, the enhancement of regenerative rates by increasing the transduced "signal strength" through reducing the inactivation of the receptor must preserve the information critical for effective regeneration. The inactivation of PTP1B by MSI-1436 ensures that many different receptors will be targeted, which we believe to be favorable since many growth factors are utilized in the complex restoration of a limb.

4. Summary of Experimental Results and Embodiments of the Invention

In summary, the present invention herein disclosed describes an unprecedented and unanticipated discovery of the stimulatory and enhancement effects of an aminosterol such as MSI-1436 on the regeneration of certain tissues in the zebrafish.

MSI-1436 treated animals exhibited ~200% greater regenerated length when compared to the control or squalamine microinjected group, when evaluated at time point prior to full repair of the tail.

In other words, the rate of regeneration was 200% greater for those animals receiving MSI-1436 than those that had received either phosphate buffered solution (PBS) or squalamine.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

Methods of Treatment

Embodiments of the invention are provided for enhancing or stimulating the regeneration of tissues including as non-limiting examples, limbs and organs in a subject. It is possible to treat diseases, disorders, trauma or other conditions where regenerative restoration of tissues would be beneficial, such as those involving the liver, skin, soft tissues and muscle, heart, nervous system, intestines, hematopoietic and vascular system. The objective is to enhance the rate and healing capacity of these tissues.

Regenerating these tissues in a subject involve identifying a subject having tissue injury and administering a therapeutically effective amount of an aminosterol such as MSI-1436 or a pharmaceutically acceptable salt thereof and/or an additional active agent to subjects having the tissue injury. It is now possible in view of the new discoveries to administer to subjects having a disorder, disease, trauma or condition (e.g., cirrhosis, hepatitis, muscular dystrophy, neurogenic myopathies, type I diabetes mellitus,) as the result of an injury to a tissue a therapeutically effective amount of an aminosterol e.g., MSI-1436 or pharmaceutically acceptable salt thereof. Such administration can ultimately stimulate or enhance tissue including as non-limiting examples, limb and/or organ regeneration from a tissue injury that occurs and therefore treat the disorder, disease, trauma or condition. Treatments of these disorders, diseases, traumas or conditions are possible where regenerative restoration of tissues would be beneficial, such as those involving the liver, skin, soft tissues, and muscle, heart, nervous system, intestines, hematopoietic and vascular system. Subjects in these embodiments are preferably mammal, and even more preferably human, and targeted tissue may be selected from liver tissue, skin soft tissues, skeletal muscle, cardiac muscle, vascular tree, central and peripheral nervous system, gastrointestinal tract, exocrine and endocrine pancreas, skeletal system, and hematopoietic tissues.

In certain embodiments of the invention, the aminosterol is an isomer of MSI-1436. The aminosterol may comprise a sterol nucleus and a polyamine, attached at any position on the sterol, such that the molecule exhibits a net charge of at least +1, the charge being contributed by the polyamine.

In other embodiments of the invention, the aminosterol is modified to include one or more of the following: (1) substitutions of the sulfate by a sulfonate, phosphate, carboxylate, or other anionic moiety chosen to circumvent metabolic removal of the sulfate moiety and oxidation of the cholesterol side chain; (2) replacement of a hydroxyl group by a non-metabolizable polar substituent, such as, for example, a fluorine atom, to prevent its metabolic oxidation or conjugation; and (3) substitution of various ring hydrogen atoms to prevent oxidative or reductive metabolism of the steroid ring system. Yet, in other embodiments of the invention, the aminosterol is a derivative of MSI-1436 modified through medical chemistry techniques known to one or ordinary skill in the art to improve bio-distribution, ease of administration, metabolic stability, or any combination thereof.

In the embodiments described herein, therapeutically effective amounts of MSI-1436 from about 0.1 to about 20-mg/kg-body weight (equivalent to about 0.07 mg/kg to about 2.67 mg/kg body weight in a human) were shown to regenerate tissue and limbs. More preferably, therapeutically effective amounts of MSI-1436 include doses from about 0.1 to 10 mg/kg-body weight (equivalent to about 0.07 mg/kg to about 1.33 mg/kg body weight in a human) and most preferably, therapeutically effective amounts of MSI-1436 include doses from about 0.1 to 5 mg/kg-body weight (equivalent to about 0.07 mg/kg to about 2.67 mg/kg body weight in a human). An additional active agent can be administered in combination with MSI-1416. Active agents include, but are not limited to, anti-infective agents, anti-inflammatory compounds, hematopoietic growth factors, anti-metabolites such as those used in cancer, pain medications, anti-emetics, anti-hypertensive agents, and cholesterol lowering agents. The amount of active agent will vary depending on many factors, including, but not limited to the severity of the tissue including as non-limiting examples, the limb or organ degeneration, the size of injury, the location of injury, the age, sex, and immune status of the subject. Various factors known to those skilled in the art affect the actual therapeutic amounts used in vivo, especially in humans. The aminosterol such as, for example, the MSI-1436 can also be administered in combination with at least one additional active agent such as one of the known growth factors (e.g., hematopoietic, epithelial, platelet derived, or vascular growth factors) to achieve either an additive or synergistic effect. The active agent can be administered (a) concomitantly; (b) as an admixture; (c) separately and simultaneously or concurrently; or (d) separately and sequentially. In certain embodiments, the aminosterol e.g., MSI-1436 is administered in the form of a liquid, capsule, tablet, intravenously, intraperitoneally, inhaled, or topically.

Pharmaceutical Compositions or Formulations and Administration

The "therapeutic agents" (e.g., aminosterols such as MSI-1436) may be present in the pharmaceutical compositions in the form of pharmaceutically acceptable salts of pharmaceutically acceptable acids and bases. They may be present in amorphous form or in crystalline forms, including hydrates and solvates. Preferably, the pharmaceutical compositions comprise a therapeutically effective amount.

Pharmaceutically acceptable salts of the therapeutic agents described herein include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining pharmaceutically acceptable acid addition salts. Salts derived from appropriate bases include alkali metal (e.g., sodium and potassium), alkaline earth metal (e.g., magnesium), ammonium and salts.

The therapeutic agents of the present invention are also meant to include all stereochemical forms of the therapeutic agents (i.e., the R and S configurations for each asymmetric center). Therefore, single enantiomers, racemic mixtures, and diastereomers of the therapeutic agents are within the scope of the invention. Also within the scope of the invention are steric isomers and positional isomers of the therapeutic agents.

In a preferred embodiment, the therapeutic agents of the present invention are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the therapeutic agent with which it is formulated.

Pharmaceutically acceptable carriers, adjuvants or vehicles that may be used in the compositions of this invention encompass any of the standard pharmaceutically accepted liquid carriers, such as a phosphate-buffered saline solution, water, as well as emulsions such as an oil/water emulsion or a triglyceride emulsion. Solid carriers may include excipients such as starch, milk, sugar, certain types of clay, stearic acid, talc, gums, glycols, or other known excipients. Carriers may also include flavor and color additives or other ingredients. The formulations of the combination of the present invention may be prepared by methods well-known in the pharmaceutical arts and described herein. Exemplary acceptable pharmaceutical earners have been discussed above.

The pharmaceutical compositions of the present invention are preferably administered intraperitoneally, or orally, preferably as solid compositions. However, the pharmaceutical compositions may be administered parenterally, by inhalation spray, topically, rectally, nasally, buccally, vaginally or via an implanted reservoir. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The pharmaceutical compositions employed in the present invention may be orally administered in any orally acceptable dosage form, including, but not limited to, solid forms such as capsules and tablets. In the case of tablets for oral use, carriers commonly used include microcrystalline cellulose, lactose and cornstarch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The pharmaceutical compositions employed in the present invention may also be administered by nasal aerosol or inhalation. Such pharmaceutical compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Should topical administration be desired, it can be accomplished using any method commonly known to those skilled in the art and includes but is not limited to incorporation of the pharmaceutical composition into creams, ointments, or transdermal patches.

The passage of agents through the blood-brain barrier to the brain can be enhanced by improving either the permeability of the agent itself or by altering the characteristics of the blood-brain barrier. Thus, the passage of the agent can be facilitated by increasing its lipid solubility through chemical modification, and/or by its coupling to a cationic carrier. The passage of the agent can also be facilitated by its covalent coupling to a peptide vector capable of transporting the agent through the blood-brain barrier. Peptide transport vectors known as blood-brain barrier permeabilizer compounds are disclosed in U.S. Pat. No. 5,268,164. Site-specific macromolecules with lipophilic characteristics useful for delivery to the brain are disclosed in U.S. Pat. No. 6,005,004.

Examples of routes of administration include parenteral, e.g., intravenous, intradermal, subcutaneous, inhalation, transdermal (topical), transmucosal, and rectal or oral administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic. Pharmaceutical compositions suitable for injection include sterile aqueous solutions (where water soluble) or dispersions and sterile powders for the extemporaneous preparation of sterile injectable solutions or dispersions. For intravenous administration, suitable carriers comprise physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, isotonic agents are included in the composition, for example, sugars, polyalcohols such as manitol, sorbitol, or sodium chloride. Prolonged absorption of an injectable composition can be achieved by including in the composition an agent that delays absorption, for example, aluminum monostearate or gelatin.

Sterile injectable solutions can be prepared by incorporating the active compound in the specified amount in an appropriate solvent with one or a combination of ingredients enumerated above, as needed, followed by filtered sterilization. Generally, dispersions are prepared by incorporating the active compound into a sterile vehicle that contains a basic dispersion medium and other ingredients selected from those enumerated above or others known in the art. In the case of sterile powders for the preparation of sterile injectable solutions, the methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can include any of the following ingredients, or compounds of a similar nature: a binder such as microcrystalline cellulose, gum tragacanth or gelatin; an excipient such as starch or lactose, a disintegrating agent such as alginic acid, Ptimogel, or cornstarch; a lubricant such as magnesium stearate or sterotes; a glidant such as colloidal silicon dioxide; a sweetening agent such as sucrose or saccharin; or a flavoring agent such as peppermint.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be pemeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Pharmacological Effects of Aminosterol 1436 Administration on the Zebrafish Appendage The purpose of this example was to evaluate the pharmacological effect of aminosterol MSI-1436 administration on the regeneration of the caudal or tail fins of zebrafish. Wildtype adult zebrafish were treated with MSI-1436 or squalamine or a control of phosphate buffered saline solution (PBS) over a four-day period via daily intraperitoneal microinjections. The adult zebrafish were bred and housed in the Yin laboratory at Mount Desert Island Biological Laboratory. The microinjections of PBS, squalamine and MSI-1436 were performed for the duration of the experiments at concentrations of 0.125 mg/kg which corresponds to 50 ng/300 mg body weight which translates to 5-200 mg per dose in humans. On average, a 5 ul volume of 10 ug/ml solution was delivered into each animal with a custom made 10 ul glass syringe (Hamilton part #80008).

The tail or caudal fins were amputated following the second day of intraperitoneal microinjections. These amputations were accomplished using a razor blade to remove approximately 50% of the caudal fins each in a manner perpendicular to the direction of bony ray growth. The zebrafish were maintained at standard conditions of 28° C. at all times during the experiments. At 4 days post-amputation (4 dpa) through 14 dpa, caudal fins were imaged with an Olympus MVX10 stereomicroscope and the length of regenerated tissue from the amputation plane was quantified using Adobe Photoshop.

Figure 2:
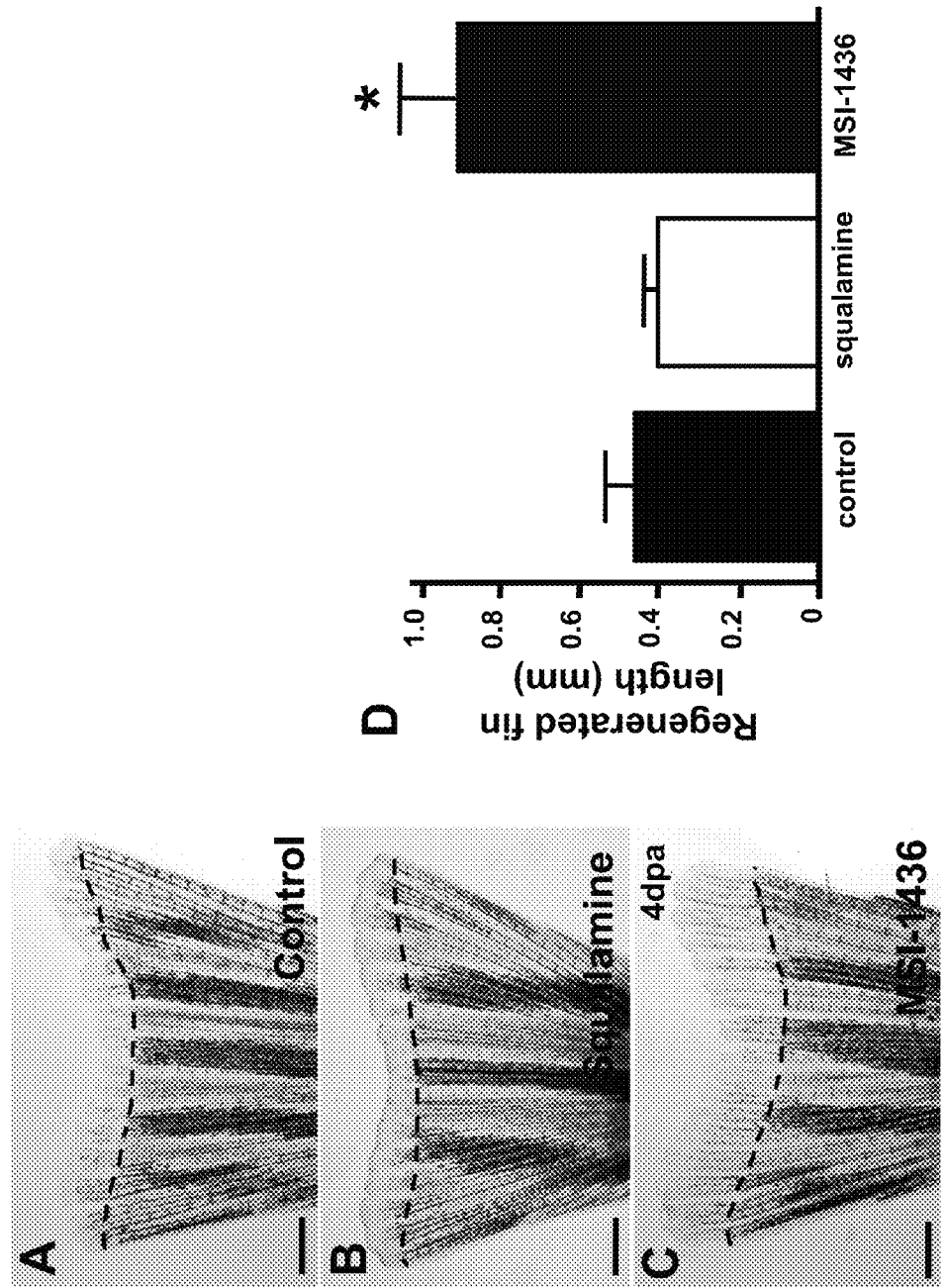
FIG. 2 shows the effect of aminosterol MSI-1436 on the regeneration of the caudal fin of adult zebrafish.

FIG. 2 shows the experimental results. (The dashed lines correspond to the amputation planes; the scale bar is 1 mm; * corresponds to the Student's ttest p-value <0.01; error bars correspond to SEM; n corresponds to 8-10 fish per group.) MSI-1436 stimulated appendage regeneration 2-fold four days after amputation (4 dpa), as shown in FIG. 2. MSI-1436 treated animals exhibited approximately 200% greater regenerated length when compared to the control and the squalamine microinjected groups, when evaluated at 4 days post-amputation (4 dpa) prior to full repair of the tail. In other words, the rate of regeneration was 200% greater for those animals receiving MSI-1436 than for those receiving either phosphate buffered saline (PBS) or squalamine. Each of the experiments was conducted with at least 6 animals per group. Each experiment was repeated four times and each time, the same enhancement of regeneration was observed in the caudal fins of the adult zebrafish. FIG. 1 reflects the results of all four experiments. Although the rate of regeneration was increased by the administration of MSI-1436, the restored tail was anatomically normal.

Figure 3:
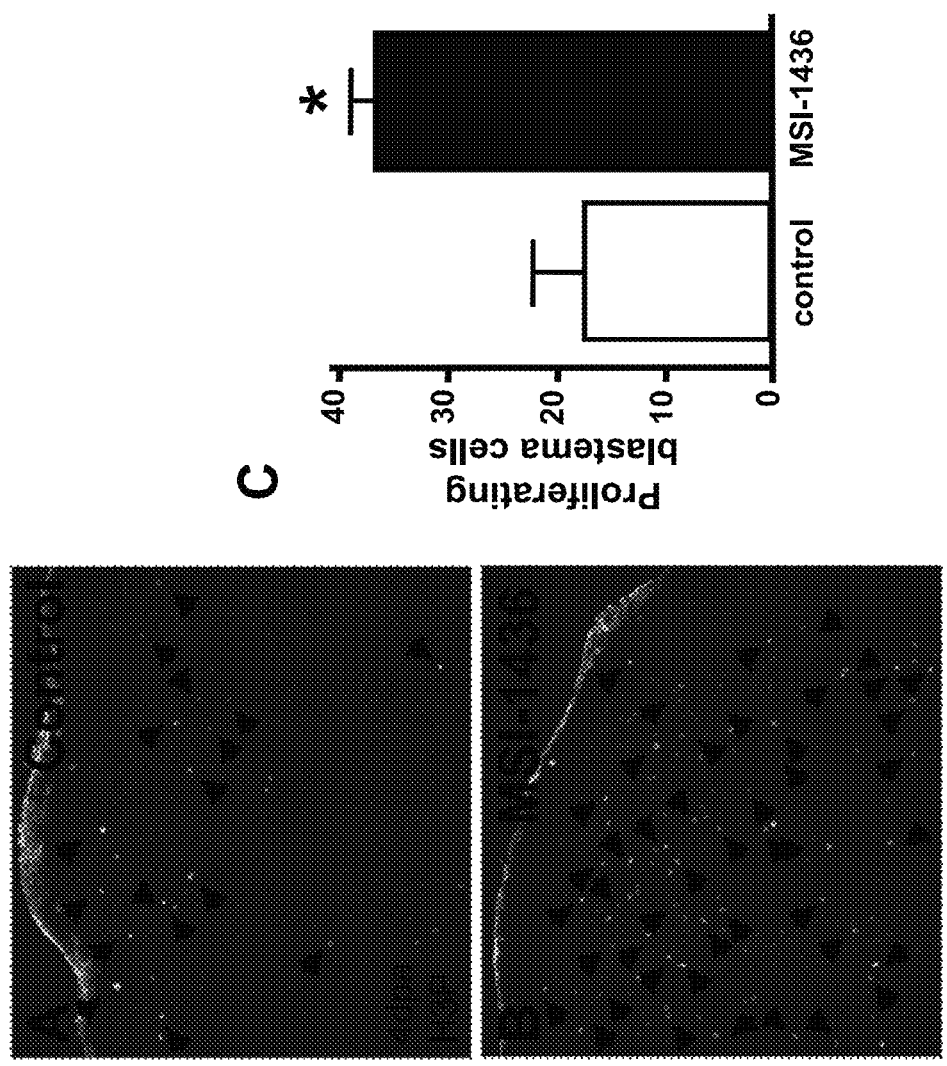
FIG. 3 shows the effect of MSI-1436 on the proliferation of reprogrammed caudal fin blastema cells in adult zebrafish.

The zebrafish caudal fins from the control and MSI-1436 treated animals were extracted at four days post-amputation (4 dpa) and stained with an antibody directed against phosphorylated histone 3 (H3P) as a marker of cell proliferation. FIG. 3 shows the results of this study. (Arrowheads highlight subset of H3P positive cells; * corresponds to Student's ttest p-value <0.001; error bars correspond to SEM; n corresponds to 6 fish per group). The blastema cells of MSI-1436 treated caudal fins demonstrated a significant 2-fold increase in cellular proliferation.

Figure 4:
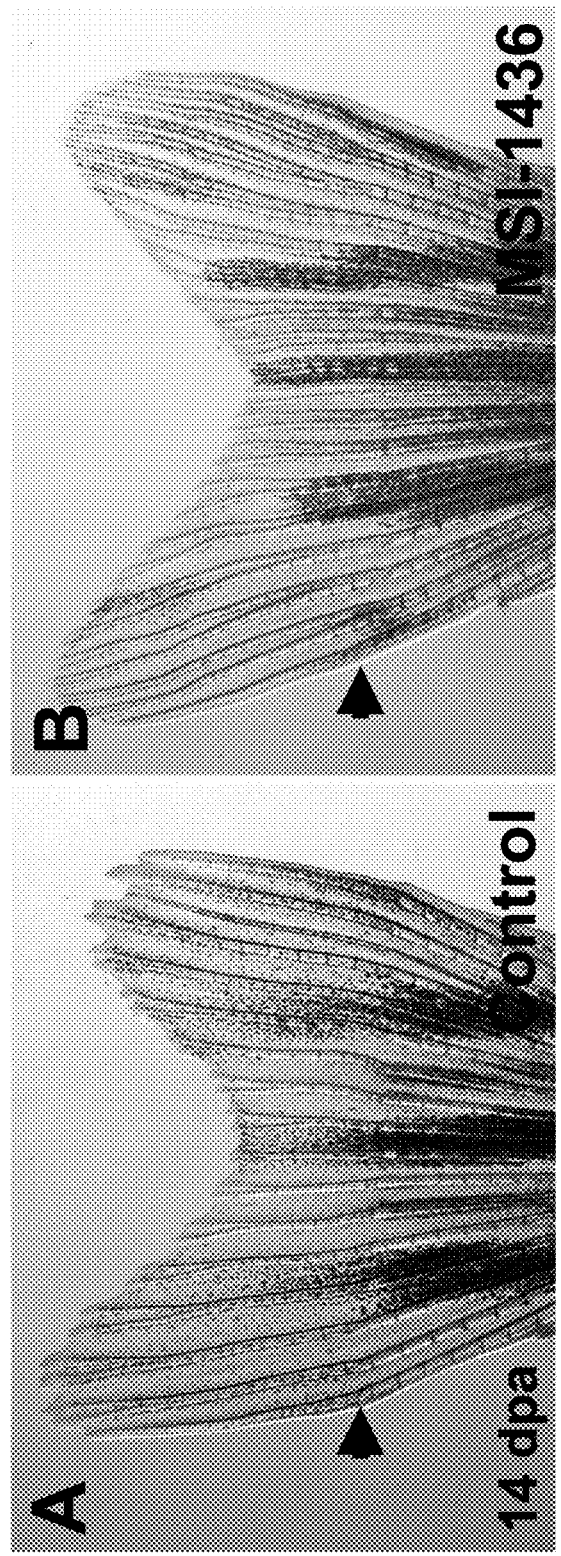
FIG. 4 shows the effect of long-term MSI-1436 exposure on tissue overgrowth in the caudal fin of adult zebrafish.

Wildtype adult zebrafish were subjected to caudal fin amputation and treated daily with either control PBS or MSI-1436 as described above in the context of FIG. 1 for 14 consecutive days during regeneration. The results of this study are shown in FIG. 4. (Arrowhead=amputation plane; n=4-6 per group). At the end of 14 days of microinjections, the MSI-1436 treated animals did not display any overgrowth of the regenerated tissue, as shown in FIG. 4. By all measurements, the MSI-1436-treated and control groups displayed the same amount of regenerated tissue at 14 days post-amputation (14 dpa), a time when zebrafish tail regeneration is normally completed.

Example 2

Pharmacological Effects of Administration on the Injured Zebrafish Heart

The pharmacological effect of aminosterol MSI-1436 administration on the regeneration of zebrafish adult hearts was tested using the same experimental paradigm described under the first study of example 1.

Figure 5:
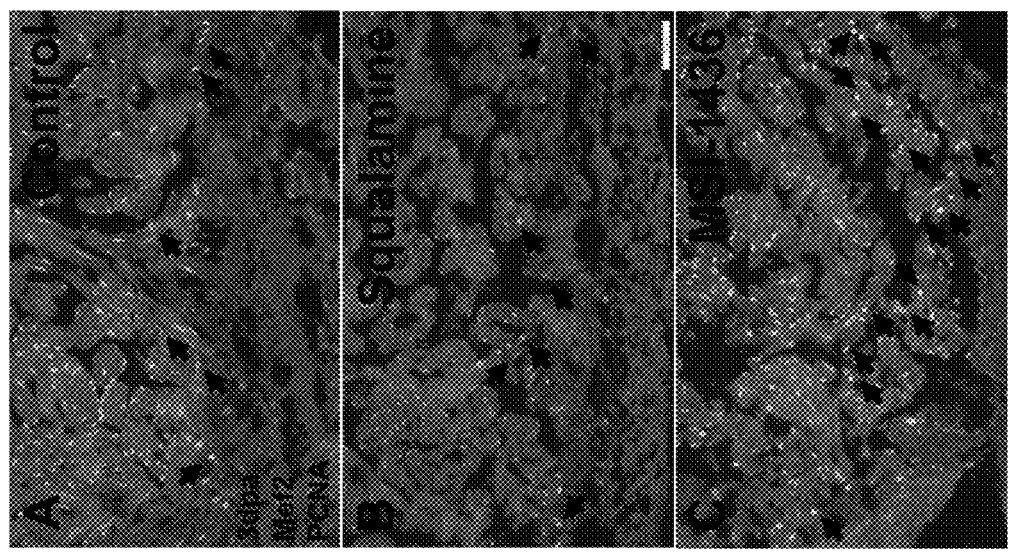
FIG. 5 shows the effect of MSI-1436 on cardiomyocyte regenerative proliferation in adult zebrafish.
Figure 5:
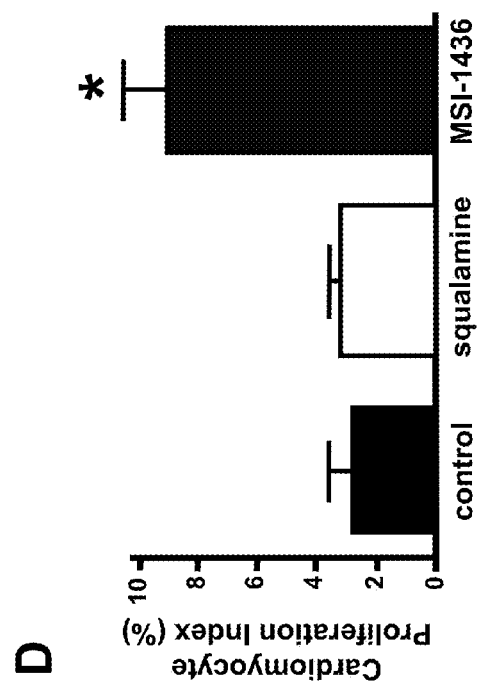

Adult zebrafish of 6-8 months old, were subjected to partial ventricular resection procedures followed by daily treatments with intraperitoneal microinjections of PBS (control) or squalamine or MSI-1436 at concentrations of 0.125 mg/kg. The ventricular resection procedures removed ~20% of the ventricular apex of each heart and challenged each animal to regenerate new heart tissue. At three days post-amputation (3 dpa), hearts were extracted, fixed, cyrosectioned and stained with antibodies directed against Mef2 and PCNA. Cardiomyocyte proliferation indices were determined for each group by representing Mef2+PCNA+cells as a percent of total Mef2+cells within each heart. The results of this study are shown in FIG. 5. (*=Student's ttest p-value <0.05; error bars=SEM; n=4 per group). Animals treated with the MSI-1436 microinjections demonstrated ~2-3-fold greater rate of heart regeneration, as quantified by cardiomyocyte proliferation indices when compared to animals microinjected with the PBS alone or the squalamine alone, as illustrated in FIG. 5. These results were reproducible in three separate experiments of 4-6 animals per group.

Figure 6:
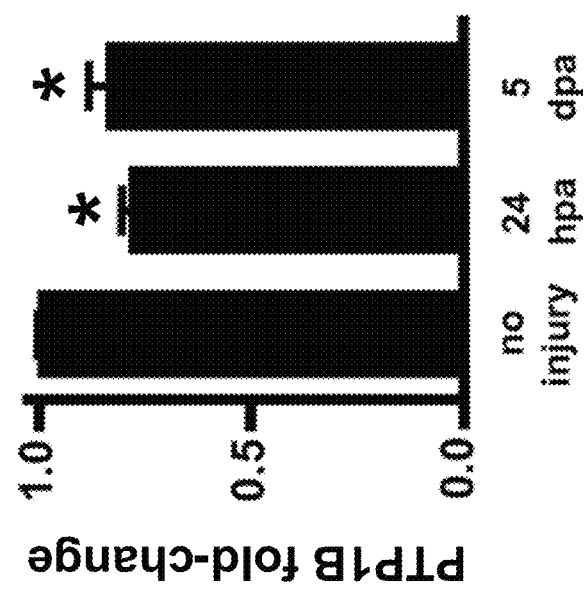
FIG. 6 shows the downregulation of the MSI-1436 target gene PTP1B in response to heart injury in adult zebrafish.

Wildtype adult zebrafish were subjected to a partial resection procedure as described above and allowed to regenerate for 24 hours post-amputation (24 hpa) or 5 days post-amputation (5 dpa) and hearts were extracted for total RNA isolation for quantitative PCR studies. The results are shown in FIG. 6. (*=Student's ttest p-value <0.05; error bars=SEM; n=4 per group) Injury to untreated adult zebrafish hearts prompted a decrease in expression of PTP1B, a known target gene regulated by MSI-1436, as depicted by FIG. 6. Levels of PTP1B significantly decreased during the early phases of heart injury, suggesting PTP1B normally functions to repress heart regeneration genetic programs.

Figure 7:
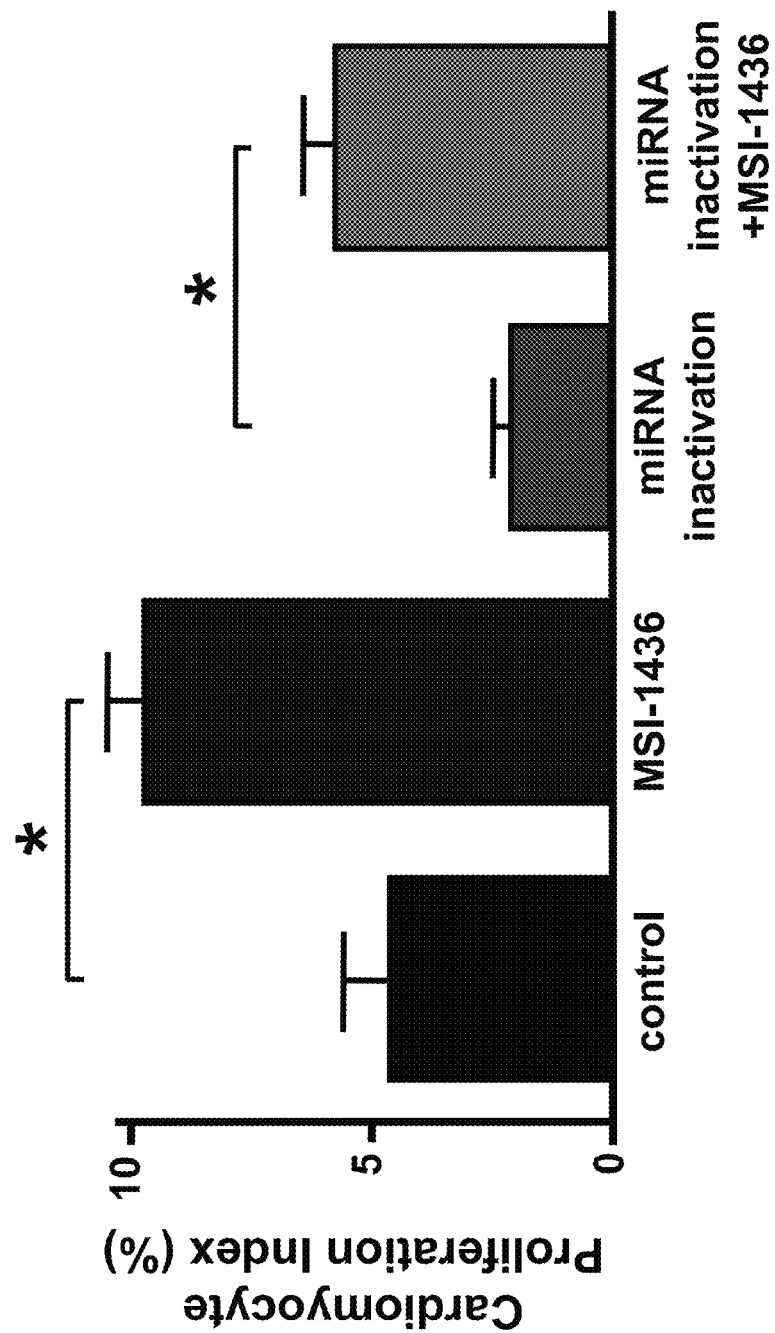
FIG. 7. shows the effect of MSI-1436 on genetically induced attenuation of cardiac regenerative proliferation in adult zebrafish hearts.

To determine if MSI-1436 is capable of rescuing defects in heart regeneration, we microinjected antisense oligonucleotides to bind and remove activity of the let-7 family of small RNAs (miRNAs). Wildtype adult zebrafish were injured via the partial ventricular resection procedure described above and treated with either 1) control of PBS, 2) MSI-1436, 3) miRNA depletion, and 4) miRNA depletion and MSI-1436. At three days post-amputation (3 dpa), hearts were extracted and stained to detect Mef2+PCNA+cells. Cardiomyocyte proliferation indices were determined as a percent of Mef2+PCNA+cells within the total cardiomyocyte population in each heart. The results of this study are shown in FIG. 7. (*=Student's ttest p-value <0.05; error bars=SEM; n=8-12 hearts per group) The inclusion of MSI-1436 enhanced cardiomyocyte proliferation indices by 2-fold when compared to control hearts. Depletion of the let-7 family of miRNAs with antisense nucleotides inhibited cardiomyocyte proliferation index by approximately 45%. In animals treated with miRNA depletion and MSI-1436, the cardiomyocyte proliferation index was restored to wildtype control levels.

Example 3

Figure 8:
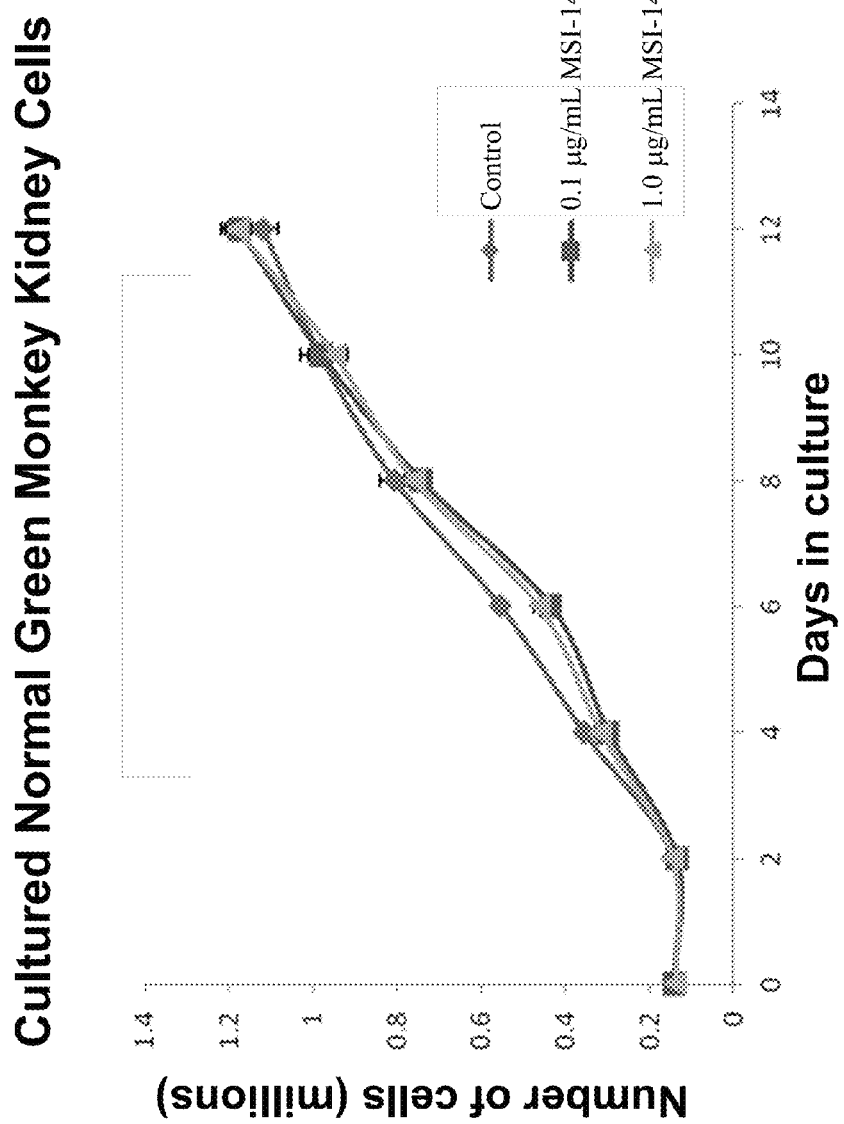
FIG. 8 shows the effect of MSI-1436 on mammalian cell proliferation.

Pharmacological Effects of Aminosterol 1436 Administration on Normal Green Monkey Kidney Cells This study was conducted to determine the effects of MSI-1436 on the cellular proliferation of normal, uninjured mammalian cells. The results of the study are shown in FIG. 8.

Normal, green monkey kidney cells were cultured with either control media of PBS or supplemented with 0.1 µg/ml or 1.0 µg/ml of MSI-1436. Growth media with and without MSI-1436 were replaced daily and total cell numbers were determined for each group over a period of 2-weeks. Cellular proliferation plots over the course of two-weeks show normal growth curves for all groups. MSI-1436 treatment did not promote overgrowth or hyperproliferation of these mammalian cells. This suggests MSI-1436 does not have aberrant proliferative activity on normal, uninjured mammalian cells.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application (including the Appendix and reference lists) are hereby expressly incorporated by reference as if set forth herein in their entirety, except where terminology is not consistent with the definitions herein. Although specific terms are employed, they are used as in the art unless otherwise indicated.

REFERENCES CITED

All citations (e.g., scientific journal publications, patents, and other reference material) mentioned herein are hereby incorporated herein by reference to the same extent as if each individual citation was specifically and individually indicated to be incorporated by reference.

1. Ahima, R. S., Patel, H. R., Takahashi, N., Qi, Y., Hileman, S. M., & Zasloff, M. A. (2002). Appetite suppression and weight reduction by a centrally active aminosterol. Diabetes, 51(7), 2099-2104.
2. Alexander, R. T., Jaumouillé, V., Yeung, T., Furuya, W., Peltekova, I., Boucher, A., Zasloff, M., et al. (2011). Membrane surface charge dictates the structure and function of the epithelial Na+/H+ exchanger. The EMBO journal, 30(4), 679-91. doi:10.1038/emboj.2010.356.
3. Bence, K. K., Delibegovic, M., Xue, B., Gorgun, C. Z., Hotamisligil, G. S., Neel, B. G., & Kahn, B. B. (2006). Neuronal PTP1B regulates body weight, adiposity and leptin action. Nat Med, 12(8), 917-924. doi:10.1038/nm1435.
4. Blum, N., & Begemann, G. (2012). Retinoic acid signaling controls the formation, proliferation and survival of the blastema during adult zebrafish fin regeneration. Development (Cambridge, England), 139(1), 107-16. doi:10.1242/dev.065391.
5. Chablais, F., & Jazwinska, A. (2010). IGF signaling between blastema and wound epidermis is required for fin regeneration. Development (Cambridge, England), 137(6), 871-9. doi:10.1242/dev.043885.
6. Curado, S., & Stainier, D. Y. R. (2010). deLiver'in regeneration: injury response and development. Seminars in liver disease, 30(3), 288-95. doi:10.1055/s-0030-1255357.
7. Frangioni, J. V., Beahm, P. H., Shifrin, V., Jost, C. A., & Neel, B. G. (1992). The nontransmembrane tyrosine phosphatase PTP-1B localizes to the endoplasmic reticulum via its 35 amino acid C-terminal sequence. Cell, 68(3), 545-560. doi:10.1016/0092-8674(92)90190-N.
8. Jazwinska, A., Badakov, R., & Keating, M. T. (2007). Activin-betaA signaling is required for zebrafish fin regeneration. Curr Biol, 17(16), 1390-1395. doi:S0960-9822(07)01697-1 [pii] 10.1016/j.cub.2007.07.019.
9. Lantz, K. a, Hart, S. G. E., Planey, S. L., Roitman, M. F., Ruiz-White, I. a, Wolfe, H. R., & McLane, M. P. (2010). Inhibition of PTP1B by trodusquemine (MSI-1436) causes fat-specific weight loss in diet-induced obese mice. Obesity (Silver Spring, Md.), 18(8), 1516-23. doi:10.1038/oby.2009.444.
10. Lee, Y., Grill, S., Sanchez, A., Murphy-Ryan, M., & Poss, K. D. (2005). Fgf signaling instructs position-dependent growth rate during zebrafish fin regeneration. Development, 132(23), 5173-5183.
11. Poss, K D, Keating, M. T., & Nechiporuk, A. (2003). Tales of regeneration in zebrafish. Dev Dyn, 226(2), 202-210.
12. Poss, Kenneth D. (2010). Advances in understanding tissue regenerative capacity and mechanisms in animals. Nature reviews. Genetics, 11(10), 710-22. doi:10.1038/nrg2879.
13. Poss, Kenneth D, Wilson, L. G., & Keating, M. T. (2002). Heart regeneration in zebrafish. Science (New York, N.Y.), 298(5601), 2188-90. doi:10.1126/science.1077857
14. Rao, M. N., Shinnar, A. E., Noecker, L. A., Chao, T. L., Feibush, B., Snyder, B., Sharkansky, I., et al. (2000). Aminosterols from the dogfish shark Squalus acanthias. J Nat Prod, 63(5), 631-635.
15. Salmi, C., Loncle, C., Vidal, N., Laget, M., Letourneux, Y., & Brunel, J. M. (2008). Antimicrobial activities of 3-amino- and polyaminosterol analogues of squalamine and trodusquemine. J Enzyme Inhib Med Chem, 23(6), 860-865. doi:10.1080/14756360701809910.
16. Selinsky, B. S., Smith, R., Frangiosi, A., Vonbaur, B., & Pedersen, L. (2000). Squalamine is not a proton ionophore. Biochim Biophys Acta, 1464(1), 135-141.
17. Selinsky, B. S., Zhou, Z., Fojtik, K. G., Jones, S. R., Dollahon, N. R., & Shinnar, A. E. (1998). The aminosterol antibiotic squalamine permeabilizes large unilamellar phospholipid vesicles. Biochim Biophys Acta, 1370(2), 218-234.
18. Sills, A. K., Williams, J. I., Tyler, B. M., Epstein, D. S., Sipos, E. P., Davis, J. D., Mclane, M. P., et al. (1998). Squalamine Inhibits Angiogenesis and Solid Tumor Growth in Vivo and Perturbs Embryonic Vasculature, 2784-2792.
19. Simons, B. D., & Clevers, H. (2011). Stem cell self-renewal in intestinal crypt. Experimental cell research, 317(19), 2719-24. doi:10.1016/j.yexcr.2011.07.010.
20. Stoick-Cooper, C. L., Weidinger, G., Riehle, K. J., Hubbert, C., Major, M. B., Fausto, N., & Moon, R. T. (2007). Distinct Wnt signaling pathways have opposing roles in appendage regeneration. Development, 134(3), 479-489. doi:dev.001123 [pii] 10.1242/dev.001123.
21. Sumioka, A., Yan, D., & Tomita, S. (2010). TARP phosphorylation regulates synaptic AMPA receptors through lipid bilayers. Neuron, 66(5), 755-67. doi:10.1016/j.neuron.2010.04.035.
22. Sánchez Alvarado, A., & Tsonis, P. A. (2006). Bridging the regeneration gap: genetic insights from diverse animal models. Nature reviews. Genetics, 7(11), 873-84. doi:10.1038/nrg1923.
23. Takahashi, N., Qi, Y., Patel, H. R., & Ahima, R. S. (2004). A novel aminosterol reverses diabetes and fatty liver disease in obese mice. J Hepatol, 41(3), 391-398.doi:10.1016/j.jhep.2004.05.006 S0168827804002119 [pii].
24. Taub, R. (2004). Liver regeneration: from myth to mechanism. Nat Rev Mol Cell Biol, 5(10), 836-847. doi:10.1038/nrm1489 nrm1489 [pii].
25. Yeung, T., Gilbert, G. E., Shi, J., Silvius, J., Kapus, A., & Grinstein, S. (2008). Membrane phosphatidylserine regulates surface charge and protein localization. Science (New York, N.Y.), 319(5860), 210-3. doi:10.1126/science.1152066.
26. Yin, V. P., Thomson, J. M., Thummel, R., Hyde, D. R., Hammond, S. M., & Poss, K. D. (2008). Fgf-dependent depletion of microRNA-133 promotes appendage regeneration in zebrafish. Genes Dev, 22(6), 728-733. doi:22/6/728 [pii] 10.1101/gad.1641808.
27. Zasloff, M, Williams, J. I., Chen, Q., Anderson, M., Maeder, T., Holroyd, K., Jones, S., et al. (2001). A spermine-coupled cholesterol metabolite from the shark with potent appetite suppressant and antidiabetic properties. Int J Obes Relat Metab Disord, 25(5), 689-697. doi:10.1038/sj.ijo.0801599.
28. Zasloff, Michael. (2002). Organisms, 415(January), 389-395.
29. Zasloff, Michael, Adams, A. P., Beckerman, B., Campbell, A., Han, Z., Luijten, E., Meza, I., et al. (2011). Squalamine as a broad-spectrum systemic antiviral agent with therapeutic potential. Proceedings of the National Academy of Sciences of the United States of America, 108(38), 15978-83. doi:10.1073/pnas.1108558108.

What is claimed is:

1. A method of treatment of a subject having cardiac muscle tissue injury, the method comprising:
administering to the subject a therapeutically effective amount of an aminosterol or a pharmaceutically acceptable salt thereof to stimulate or enhance regeneration or growth of the cardiac muscle tissue;

wherein stimulation or enhancement of regeneration or growth of the cardiac muscle tissue causes at least a partial restoration or growth of the cardiac muscle tissue;

and wherein the aminosterol is MSI-1436.

2. The method of claim 1 further comprising:

prior to the administering step, identifying a subject having the cardiac muscle tissue injury.

3. The method of claim 1, wherein the aminosterol is an isomer of MSI-1436.

4. The method of claim 1, wherein the therapeutically effective amount of the aminosterol is from about 0.07 mg/kg to about 2.67 mg/kg body weight in a human.

5. The method claim 1, wherein the therapeutically effective amount of the aminosterol is administered in combination with at least one additional active agent to achieve an additive or synergistic effect.

6. The method of claim 5, wherein the active agent is administered according to one of the administration methods consisting of:

(i) administering separately and simultaneously at least one dose of the active agent and at least one dose of the aminosterol;

(ii) administering at least one dose of an admixture including at least one dose of the active agent and at least one dose of the aminosterol;

(iii) administering separately and sequentially at least one dose of the active agent and at least one dose of the aminosterol, the at least one dose of the active agent being administered prior to administration of the at least one dose of the aminosterol; and (iv) administering separately and sequentially at least one dose of the active agent and at least one dose of the aminosterol, the at least one dose of the active agent being administered following administration of the at least one dose of the aminosterol.

7. The method of claim 1, wherein the therapeutically effective amount of aminosterol is administered in the form of a liquid, a capsule, a tablet, intravenously, intraperitoneally, inhaled, or topically.

8. The method of claim 1, wherein the subject is a mammal.

9. The method of claim 1, wherein the subject is a human.

* * * * *

UNITED STATES PATENT AND TRADEMARK OFFICE
CERTIFICATE OF CORRECTION

PATENT NO. : 9,504,700 B2
APPLICATION NO. : 14/137259
DATED : November 29, 2016
INVENTOR(S) : Michael Alan Zasloff et al.

Page 1 of 1

It is certified that error appears in the above-identified patent and that said Letters Patent is hereby corrected as shown below:

In the Specification

Regarding the STATEMENT REGARDING FEDERALLY SPONSORED RESEARCH OR DEVELOPMENT, the term "N/A" should be deleted and replaced with the following statement: "This invention was made with government support under contract number W81XWH-11-1-0425 awarded by U.S. Army Medical Research and Material Command (ARMY/MRMC); and contract numbers P20 GM104318 and P20 GM103423 each awarded by National Institutes of Health (NIH). The government has certain rights in the invention."

Signed and Sealed this
Eighth Day of August, 2017

Joseph Matal
*Performing the Functions and Duties of the
Under Secretary of Commerce for Intellectual Property and
Director of the United States Patent and Trademark Office*